(12) United States Patent
Erdelen et al.

(10) Patent No.: US 6,218,407 B1
(45) Date of Patent: Apr. 17, 2001

(54) INSECTICIDES

(75) Inventors: Christoph Erdelen, Leichlingen; Wolfgang Krämer, Burscheid; Kai-Uwe Brüggen, Sprockhövel, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/488,090

(22) Filed: Jan. 20, 2000

Related U.S. Application Data

(62) Division of application No. 09/360,971, filed on Jul. 27, 1999, now Pat. No. 6,060,489, which is a division of application No. 08/952,359, filed as application No. PCT/EP96/02039 on May 13, 1996, now Pat. No. 5,994,331.

(30) Foreign Application Priority Data

May 24, 1995 (DE) ................................. 195 19 007

(51) Int. Cl.⁷ ............................. A01N 43/40; A01N 53/00
(52) U.S. Cl. ........................................... 514/341; 514/531
(58) Field of Search ..................... 514/341, 531

(56) References Cited

U.S. PATENT DOCUMENTS 4,849,432  7/1989  Shiokawa et al. ................... 514/341

FOREIGN PATENT DOCUMENTS

| | | |
|---|---|---|
| 0 387 663 | 9/1990 | (EP) . |
| 2720230 | 5/1995 | (FR) . |
| 63-126805 | 5/1988 | (JP) . |
| 63-126806 | 5/1988 | (JP) . |
| 63-126810 | 5/1988 | (JP) . |
| 3-7206 | 1/1991 | (JP) . |
| 4-112804 | 4/1992 | (JP) . |
| 4-112805 | 4/1992 | (JP) . |
| 4-120007 | 4/1992 | (JP) . |
| 6-227909 | 8/1994 | (JP) . |
| 6-298609 | 10/1994 | (JP) . |
| 93/00009 | 1/1993 | (WO) . |
| 95/33380 | 12/1995 | (WO) . |
| 96/10915 | 4/1996 | (WO) . |
| 96/17520 | 6/1996 | (WO) . |
| 96/23411 | 8/1996 | (WO) . |

OTHER PUBLICATIONS

The Pesticide Manual 10th edition, (month unavailable) 1994. Tom Liw pp. 953 & 954.
R. Wegeler (Ed.) K. Naumann, "Chemie der Pflanzenschutz- und Schädlingsbekämpfungsmittel", Band 7, Chemie der synthetischen Pyrethroid–Insektizide (month unavailable) 1981.

*Primary Examiner*—Allen J. Robinson
(74) *Attorney, Agent, or Firm*—Joseph C. Gil

(57) ABSTRACT

The present invention relates to insecticidal mixtures of chloronicotinyl insecticides of the formula (I)

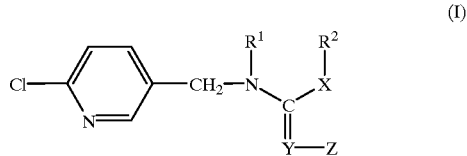

in which
$R^1$ represents $C_1$–$C_5$-alkyl,
$R^2$ represents hydrogen or $C_1$–$C_5$-alkyl
or
$R^1$ and $R^2$ together represent —$CH_2$—$CH_2$—; —$CH_2$—$CH_2$—$CH_2$— or

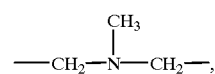

X represents an NH group, $NCH_3$ group or represents sulphur,
Y represents nitrogen or a CH group and
Z represents cyano or nitro, with one or more of the synergists mentioned in the description.

4 Claims, No Drawings

INSECTICIDES

This is a divisional application of Ser. No. 09/360,971, filed on Jul. 27, 1999 and now U.S. Pat. No. 6,060,489, which was a divisional application of Ser. No. 08/952,359, filed on Nov. 17, 1997 and is now U.S. Pat. No. 5,994,331 which is a 371 of PCT/EP96/02039, filed May 13, 1996.

TECHNICAL FIELD OF THE INVENTION

The present invention relates to insecticidal compositions based on chloronicotinyl insecticides and synergists for insecticides.

BACKGROUND OF THE INVENTION

Chloronicotinyl insecticides are known, for example from EP-OS (European Published Application) 192 060.

Synergists for insecticides are inhibitors of oxidases or cytochrome P 450 or increase the penetrability of cell membranes. They are known, for example, from Chemie der Pflanzenschutz-und Schädlingsbekämpfungsmittel Volume 7K. Naumann Chemie der Synthetischen Pyrethroid-Insektizide Springer Verlag 1981 pages 3–5.

DETAILED DESCRIPTION OF THE INVENTION

The present invention relates to mixtures of chloronicotinyl insecticides of the formula (I)

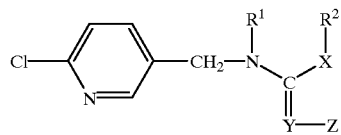

in which $R^1$ represents $C_1$–$C_5$-alkyl, $R^2$ represents hydrogen or $C_1$–$C_5$-alkyl or $R^1$ and $R^2$ together represent —$CH_2$—$CH_2$—; —$CH_2$—$CH_2$—$CH_2$— or

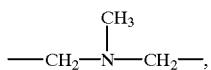

X represents an NH group, $NCH_3$ group or represents sulphur,

Y represents nitrogen or a CH group and

Z represents cyano or nitro, with one or more synergists from the group consisting of
O,O-dimethyl S-(4-oxo-1,2,3-benzotriazine-3-methyl) dithiophosphate [M-Gusathion];
O-ethyl O-(4-bromo-2-chlorophenyl)-s-#N-propyl thiophosphate [Curacron];
3,5-dimethyl-4-methylthiophenyl N-methylcarbamate [Mesurol];
4-bromo-2-(4-chlorophenyl)-2-(ethoxymethyl)-5-(trifluoromethyl)-1H-pyrrole-3-carbonitrile [AC 303, 630];
O,S-dimethyl phosphoamidothioate [Tamaron]N-[2,6-bis(-1-methylethyl)-4-phenoxyphenyl]-N'-(1,1-dimethylethyl)-thiourea [CGA 106 630; Polo];
abamectin;
ethyl (3-t-butyl-1-dimethylcarbamoyl-1H-1,2,4-triazol-5-ylthio)-acetate [Triazuron];
6,7,8,9,10,10-hexachloro-1,5,5A,6,9,9A-hexahydro-6,9-methane-2,4,3-benzodioxathiepine 3-oxide [Endosulfan; Thiodan];
trans-5-(4-chlorophenyl)-N-cyclohexyl-4-methyl-2-oxo-3-thiazolidine-carboxamide [Cesar; Hexythiazox];
3,6-bis-(2-chlorophenyl)-1,2,4,5-tetrazine [Clofentezin; Apollo];
ethyl [2-(4-phenoxyphenoxy)-ethyl]carbamate [Fenoxycarb; Insegar];
2-[1-methyl-2-(4-phenoxyphenoxy)ethoxy]pyridine [Pyriproxyfen; Tiger];
N-cyclopropyl-1,3,5-triazine-2,4,6-triamine [Cyromazine];
benzoic acid [-2-benzoyl-1-(1,1-dimethyl)]hydrazide [RH 5849];
5-amino-3-cyano-1-(2,6-dichloro-4-trifluoromethylphenyl)-4-trifluoromethylthionopyrazole [Fipronil];
cis-(2,3,5,6-tetrafluoro-4-methylphenyl)methyl-$^3$-(2-chloro-3,3,3-trifluoro-1-propenyl)-2,2-dimethyl-cyclopropane-carboxylate [Tefluthrin; Force];
1,5-bis-(2,4-dimethylphenyl)-3-methyl-1,3,5-triazapenta-1,4-dione [Amitraz];
3,5-dimethylbenzoic acid 1-(1,1-dimethylethyl)-2-(4-ethylbenzoyl)hydrazide [RH 5992];
N-[[2,5-dichloro-4-(1,1,2,3,3,3-hexafluoropropoxy) phenyl]-aminocarbonyl]-2,6-difluorobenzamide [Match];
(4-ethoxyphenyl)-[3-(4-fluoro-3-phenoxyphenyl) propyl]dimethylsilane [HOE 498];
and/or
(E)-4,5-dihydro-6-methyl-4-[(3-pyridinylmethylene) amino]-1,2,4-triazin-3-(2H)-one [Chess].

Preference is given to novel mixtures of the above specified synergists with chloronicotinyl insecticides of the following structural formulae:

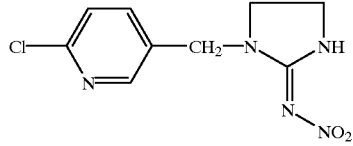

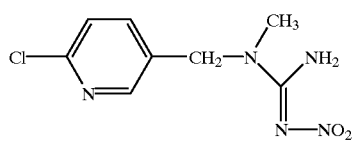

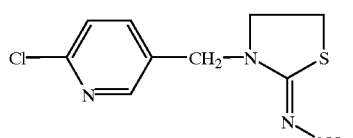

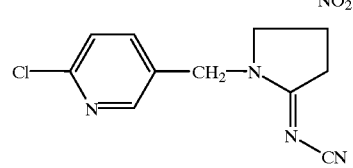

-continued

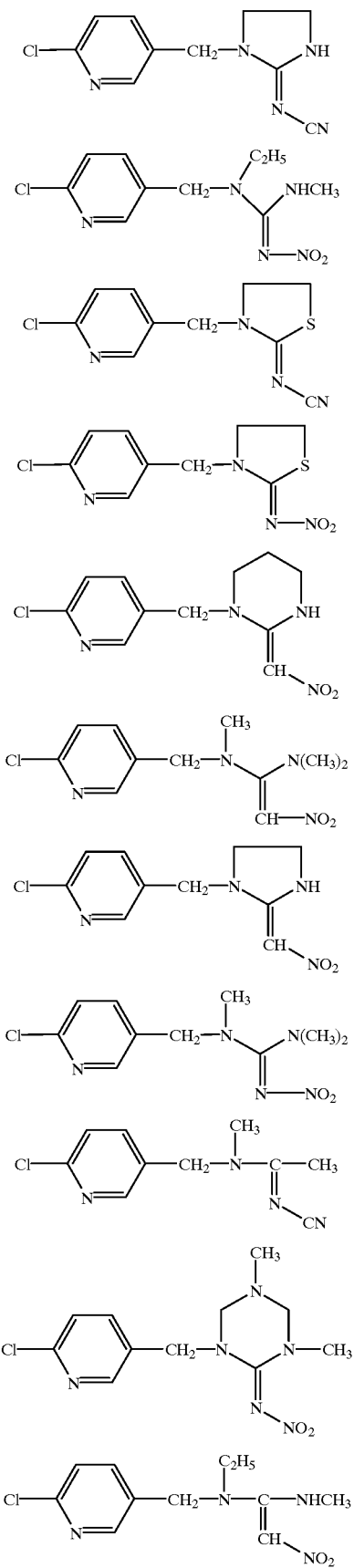

-continued

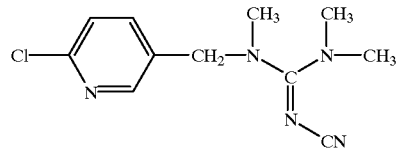

Particular preference is given to novel mixtures of the abovementioned synergists with chloronicotinyl insecticides of the formulae:

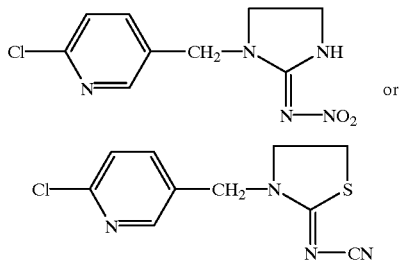

The novel active compound mixtures of chloronicotinyl insecticides with the above-specified synergists can be converted into the customary formulations, such as solutions, emulsions, suspensions, powders, foams, pastes, granules, aerosols, active-compound-impregnated natural and synthetic materials, very fine encapsulations in polymeric substances and in coating compositions for seed, furthermore in formulations with smokes, such as fumigating cartridges, fumigating cans, fumigating coils and the like, and also ULV cold mist and warm mist formulations.

These formulations are prepared in a known manner, for example by mixing the active compounds with extenders, that is, liquid solvents, pressurized liquefied gases and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellant, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates as dispersing agents there are suitable: for example lignin-sulphite waste liquors and methylcellulose.

Adhesives such as carboxy-methylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1and 95per cent by weight of active compound composition, preferably between 0.5and 90%.

The active compound mixtures are suitable for combating animal pests, in particular insects, arachnids and nematodes, encountered in agriculture, in forestry, in the protection of stored products and of materials, and in the hygiene field, and have good plant tolerance and favourable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis and Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi, Phylloxera vastatrix,* Pemphigus spp., Empoasca spp., *Euscelis bilobatus, Nephotettix cincticeps, Lecanium comi, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and Tipula paludosa.

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., Trichodorus spp.

The active compound mixtures according to the invention can be present in their commercially available formulations and in use forms prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

In the Examples which follow, imidacloprid, of the formula below

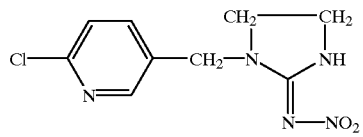

is used as insecticidally active compound from the group of the chloronicotinyl insecticides.

EXAMPLE A

Phaedon Larvae Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and have mustard beetle larvae (*Phaedon cochleariae*) placed on them while the leaves are still moist. After the desired period of time, the plants have mustard beetle larvae (*Phaedon cochleariae*) placed on them. After in each case 7 days, the kill in % is determined. 100% means that all the beetle larvae have been killed; 0% means that none of the beetle larvae have been killed.

0.02% of the synergist was admixed in each case to the particular test concentration of imidacloprid. In this test, a synergistic action was shown, for example, by the following mixtures:

TABLE A

| | (plant-injurious insects) Phaedon larvae test | |
|---|---|---|
| Active compounds | Active compound concentration in % | Kill in % after 7 days |
| Imidacloprid | 0.0008 | 5 |
| M-Gusathion | 0.0008 | 40 |
| Imidacloprid + M-Gusathion | 0.0008 + 0.0008 | 95 |
| HOE 498 | 0.008 | 35 |
| Imidacloprid + HOE 498 | 0.0008 + 0.0008 | 100 Curacron |
| Curacron | 0.0008 | 15 |
| Imidacloprid + Curacron | 0.0008 + 0.0008 | 70 |

EXAMPLE B

Plutella Test (BLT resistance)

Solvent: 7 parts by weight of dimethylformamide

Emulsifier: 1 part by weight of alkylaryl polyglycol ether

To produce a suitable preparation of active compound, 1 part by weight of active compound is mixed with the stated amount. of solvent and the stated amount of emulsifier, and the concentrate is diluted with water to the desired concentration.

Cabbage leaves (*Brassica oleracea*) are treated by being dipped into the preparation of active compound of the desired concentration and have caterpillars of the diamondback moth (*Plutella maculipennis*, BLT resistance) placed on them while the leaves are still moist.

After the desired period of time, the kill in % is determined. 100% means that all the caterpillars have been destroyed; 0% means that none of the caterpillars have been destroyed.

0.02% of the synergist was admixed in each case to the particular test concentration of imidacloprid. In this test, a synergistic action was shown, for example, by the following mixtures:

TABLE B

| | (plant-injurious insects) Plutella test (resistant) | |
|---|---|---|
| Active compounds | Active compound concentration in % | Kill in % after 7 days |
| Imidacloprid | 0.004 | 0 |
| M-Gusathion | 0.0008 | 0 |
| Imidacloprid + M-Gusathion | 0.004 + 0.0008 | 100 |
| HOE 498 | 0.0008 | 0 |
| Imidacloprid + HOE 498 | 0.004 + 0.0008 | 100 |
| Curacron | 0.0008 | 40 |
| Imidacloprid + Curacron | 0.004 + 0.0008 | 100 |
| Mesurol | 0.004 | 0 |
| Imidacloprid + Mesurol | 0.004 + 0.004 | 100 |
| Tamaron | 0.004 | 0 |
| Imidacloprid + Tamaron | 0.004 + 0.004 | 100 |
| Match | 0.0000064 | 0 |
| Imidacloprid + Match | 0.004 + 0.0000064 | 65 |

EXAMPLE C

Spodoptera Test

Solvent: 7 parts by weight of dimethylformamide Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and have caterpillars of the fall armyworm (*Spodoptera frugiperda*) placed on them while the leaves are still moist.

After the desired period of time, the kill in % is determined. 100% means that all the caterpillars have been destroyed; 0% means that none of the caterpillars have been destroyed.

0.02% of the synergist was admixed in each case to the particular test concentration of imidacloprid. In this test, a synergistic action was shown, for example, by the following mixtures:

TABLE C (plant-injurious insects)
Spodoptera frugiperda test

| Active compounds | Active compound concentration in % | Kill in % after 7 days |
|---|---|---|
| Imidacloprid | 0.004 | 50 |
|  | 0.0008 | 0 |
| AC 303.630 | 0.0008 | 0 |
| Imidacloprid + | 0.004 + | 100 |
| AC 303.630 | 0.0008 | |
| RH 5992 | 0.0008 | 0 |
| Imidacloprid + | 0.004 + | 100 |
| RH 5992 | 0.0008 | |
| Tamaron | 0.004 | 0 |
| Imidacloprid + | 0.004 + | 100 |
| Tamaron | 0.004 | |
| Match | 0.0000064 | 15 |
| Imidacloprid + | 0.004 + | 100 |
| Match | 0.0000064 | |

EXAMPLE D

Myzus Test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) which are severely infested with the green peach aphid (*Myzus persicae*) are treated by being dipped into the preparation of the active compound of the desired concentration.

After the desired period of time, the kill in % is determined. 100% means that all the aphids have been killed; 0% means that none of the aphids have been killed.

TABLE D (plant-injurious insects)
Myzus test

| Active compounds | Active compound concentration in % | Kill in % after 6 days |
|---|---|---|
| Imidacloprid | 0.00016 | 10 |
| Mesurol | 0.004 | 0 |
| Imidacloprid + | 0.00016 + | 70 |
| Mesurol | 0.004 | |
| Tamaron | 0.004 | 0 |
| Imidacloprid + | 0.00016 + | 80 |
| Tamaron | 0.004 | |

What is claimed is:

1. An insecticidal mixture comprising synergistic insecticidally effective amounts of imidacloprid

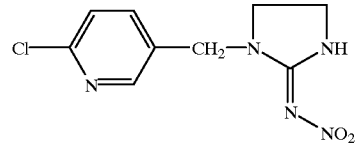

and cis-(2,3,5,6-tetrafluoro-4-methylphenyl)methyl-3-(2-chloro-3,3,3-trifluoro-1-propenyl)-2,2-dimethyl-cyclopropane-carboxylate.

2. An insecticidal composition comprising between 0.1 and 95 per cent by weight of the insecticidal mixture according to claim 1.

3. A method of combating unwanted insects, arachnids and nematodes comprising the step of administering to such insects, arachnids and nematodes or to a locus from which it is desired to exclude such insects, arachnids and nematodes a synergistic pesticidally effective amount of the mixture according to claim 1.

4. A process for preparing an insecticidal composition comprising mixing the insecticidal mixture of claim 1 with extenders, optionally using surface-active agents.

* * * * *